United States Patent
Shoseyov et al.

(10) Patent No.: US 11,117,929 B2
(45) Date of Patent: Sep. 14, 2021

(54) PURIFICATION OF AN AGENT OF INTEREST

(71) Applicant: YISSUM RESEARCH DEVELOPMENT COMPANY OF THE HEBREW UNIVERSITY OF JERUSALEM LTD, Jerusalem (IL)

(72) Inventors: Oded Shoseyov, Carmei Yosef (IL); Amit Yaari, Kibbutz Ein Dor (IL)

(73) Assignee: Yissum Research Development Company of the Hebrew University of Jerusalem Ltd.

( * ) Notice: Subject to any disclaimer, the term of this patent is extended or adjusted under 35 U.S.C. 154(b) by 70 days.

(21) Appl. No.: 16/499,012

(22) PCT Filed: Mar. 29, 2018

(86) PCT No.: PCT/IL2018/050372
§ 371 (c)(1),
(2) Date: Sep. 27, 2019

(87) PCT Pub. No.: WO2018/178991
PCT Pub. Date: Apr. 10, 2018

(65) Prior Publication Data
US 2020/0055893 A1 Feb. 20, 2020

Related U.S. Application Data

(60) Provisional application No. 62/478,111, filed on Mar. 29, 2017.

(51) Int. Cl.
C07K 14/415 (2006.01)
C12N 15/82 (2006.01)
(Continued)

(52) U.S. Cl.
CPC .............. *C07K 1/34* (2013.01); *B01D 61/142* (2013.01); *C07K 1/36* (2013.01); *C07K 14/415* (2013.01); *C12N 15/8257* (2013.01)

(58) Field of Classification Search
CPC .... C07K 1/34; B01D 61/142; C12N 15/8257; B82Y 5/00
See application file for complete search history.

(56) References Cited

U.S. PATENT DOCUMENTS 5,593,882 A * 1/1997 Erbe ....................... A61P 17/06
435/358
5,856,201 A 1/1999 Shoseyov et al.
(Continued)

FOREIGN PATENT DOCUMENTS

WO 2011094617 8/2011
WO 2005021764 3/2015

OTHER PUBLICATIONS

Shoseyov, O.; Shani, Z.; Levy, I., Carbohydrate binding modules: biochemical properties and novel applications. Microbiology and Molecular Biology Reviews 2006, 70 (2), 283-295.
(Continued)

*Primary Examiner* — Krishnan S Menon
(74) *Attorney, Agent, or Firm* — McAndrews, Held & Malloy, Ltd.

(57) ABSTRACT

A method is disclosed that exploits the combined features of carbohydrate binding modules (CBM) and nanocrystalline cellulose (CNC) for 'fishing out' specific agents of interest (AOI), such as proteins, which are optionally present or produced in culture.

19 Claims, 2 Drawing Sheets

(51) Int. Cl.
*B01D 61/14* (2006.01)
*B82Y 5/00* (2011.01)
*C07K 1/34* (2006.01)
*C07K 1/36* (2006.01)

(56) References Cited

U.S. PATENT DOCUMENTS

2011/0319294 A1* 12/2011 Arnold ............ C12Y 302/01004
                                                        506/11
2013/0337528 A1    12/2013 Thompson et al.
2015/0376229 A1* 12/2015 Blum ..................... C07K 16/18
                                                        530/387.3
2017/0292136 A1* 10/2017 Westh ....................... C12P 7/14

OTHER PUBLICATIONS

Goldstein, M. A.; Takagi, M.; Hashida, S.; Shoseyov, O.; Doi, R.; Segel, I., Characterization of the cellulose-binding domain of the *Clostridium cellulovorans* cellulose-binding protein A. Journal of bacteriology 1993, 175 (18), 5762-5768.

Charreau, H.; L Foresti, M.; Vazquez, A., Nanocellulose patents trends: a comprehensive review on patents on cellulose nanocrystals, microfibrillated and bacterial cellulose. Recent patents on nanotechnology 2013, 7 (1), 56-80.

Rebouillat, S.; Pla, F., State of the art manufacturing and engineering of nanocellulose: a review of available data and industrial applications. 2013.

Peng, B.; Dhar, N.; Liu, H.; Tam, K, Chemistry and applications of nanocrystalline cellulose and its derivatives: a nanotechnology perspective. The Canadian Journal of Chemical Engineering 2011, 89 (5), 1191-1206.

Shpigel, E.; Goldlust, a.; Eshel, a.; Ber, I. K.; Efroni, G.; Singer, Y.; Levy, I.; Dekel, M.; Shoseyov, O., Expression, purification and applications of staphylococcal Protein A fused to cellulose-binding domain. Biotechnology and applied biochemistry 2000, 31 (3), 197-203.

Marinaccio, P. J.; Repetti, R. V., Cross-flow filtration. Google Patents: 1989.

Daufin, G.; Escudier, J.-P.; Carrere, H.; Berot, S.; Fillaudeau, L.; Decloux, M., Recent and emerging applications of membrane processes in the food and dairy industry. Food and Bioproducts Processing 2001, 79 (2), 89-10.

Cheryan, M., Ultrafiltration and Microfiltration Handbook. Taylor & Francis: 1998.

Azevedo, A. M.; Rosa, P. A.; Ferreira, I. F.; Aires-Barros, M. R., Chromatographyfreerecovery of biopharmaceuticals through aqueous two-phase processing. Trends in biotechnology 2009, 27 (4), 240-247.

Thömmes, J.; Etzel, M., Alternatives to chromatographic separations. Biotechnology progress 2007, 23 (1), 42-45.

Forsgren, A.; Sjöquist, J., "Protein a" from *S. aureus* I. Pseudoimmune reaction with human γ-globulin. The Journal of Immunology 1966, 97 (6), 822-827.

Updyke, T. V.; Nicolson, G. L., Immunoaffinity isolation of membrane antigens with biotinylated monoclonal antibodies and immobilized streptavidin matrices. Journal of immunological methods 1984, 73 (1), 83-95.

Stols, L; Gu, M.; Dieckman, L.; Raffen, R.; Collart, F. R; Donnelly, M. I., A new vector for high-throughput, ligation-independent cloning encoding a tobacco etch virus protease cleavage site. Protein expression and purification 2002, 25 (1), 8-15.

Jozef Nahalka et al: "Fusion to a pull-down domain: a novel approach of . . . " vol. 97 No. 3 p. 454-461.

* cited by examiner

Figure 1A 0.2 μm HF Filtration

Retentate Discarded

Figure 1B

0.2 μm HF Filtration with added CNC added CNC

Permeate Discarded

Figure 1C  Elution by alkaline pH, only eluted POI permeates through 0.2 μm membrane Purified Product

- Large insoluble particles
- Small molecules
- Plant Proteins
- IL2-TEV-CBD
- Crystalline Nano Cellulose

Figure 1D

Elution by proteolysis, only cleaved POI permeates through 0.2 μm membrane

Figure 1E

Purified POI Bound to NCC

PURIFICATION OF AN AGENT OF INTEREST

CROSS-REFERENCE TO RELATED APPLICATIONS

The present application is a National Phase Entry of PCT International Application No. PCT/IL2018/050372, which was filed on Mar. 29, 2018, which claims priority to U.S. provisional patent application Ser. No. 62/478,111, filed Mar. 29, 2017, both of which are hereby incorporated by reference in their entireties.

TECHNOLOGICAL FIELD

The invention generally provides methods for material, e.g., protein, isolation from, e.g., liquid cell culture mixtures, using affinity binding of nanocrystalline cellulose (CNC) to protein-cellulose binding domain chimeras.

BACKGROUND OF THE INVENTION

CBMs are carbohydrate binding modules found in different organisms [1]. Cellulose Binding Domain (CBD) is one example of CBMs. CBDclos [2] is a protein domain that is isolated from the bacterium *Clostridium cellulovorans*. It strongly binds to cellulose and forms a stable but reversible linkage that can withstand shear forces and mild changes in acidic and basic pH (pH 4 to 10) and salinity (10 mM to saturated NaCl). CBD has previously been used for protein purification on cellulose columns [6]. However, the lack of available cellulose beads suitable for chromatography with high surface area, ability to withstand high flow rates and high pressure, limits its application.

Nanocrystalline cellulose (CNC or NCC)) particles are small (~300 nm), high aspect ratio crystallites that are produced from cellulose by different methods [3-5]. Each particle can bind in excess of 10 CBDclos domains. The material is non-toxic and completely safe. It is also quite stable to pH changes (1 to 13) and high shear forces. It is a cheap and a widely available material.

U.S. Pat. No. 5,856,201 [7] discloses the high affinity of cellulose binding domain (CBD) protein to crystalline cellulose and to fusion proteins of CBD and a second protein, as well as to methods of affinity separation using this fusion product.

Cross flow filtration processes are a refinement of simple (dead-end) membrane filtration processes. By creating turbulent, high shear flow perpendicular to the membrane surface they can evacuate the gel layer that forms on the membrane surface and thus improve the flux and the operation time [8]. Membrane crossflow filtrations are used on very large scales (100 of m3/day) in the food industry, for clarification and concentration of dairy products, fruit and vegetable juices, beverages, beer, wine and more. Additional large-scale applications are blood products and waste treatment [8]. Depending on membrane cutoff, crossflow filtration membranes can clarify particles from a wide range of sizes, starting from salt ions (reverse osmosis) and up to sand particles. They can also operate at very high dry solids contents (60 gt/100 $gr^{-1}$) and viscosities [9]. Membranal processes are, however, mainly used for relatively coarse, up-stream purification stages, for separation of particulates or proteins that significantly differ in size. For efficient separation, a size difference of 1 order of magnitude (10 fold) between the separated entities is required [10]. This limits the method from being used for down-stream purifications and polishing, were separation a specific entity from a population of similarly sized proteins or particles is required.

Chromatographic separation processes (column chromatography) are utilized where high purity and therefore high selectivity is required and are basically the workhorse of protein separation in the biopharmaceutical industry. However, chromatographic processes are expensive (accounting for >70% of the total downstream costs [11]), lengthy and require complex upstream preparations. Due to their cost and complexity of scale up, they are less suitable for high volume processes. As the need for large quantities of high purity proteins expand, the demand for alternative purification methods is increasing [12].

REFERENCES

[1] Shoseyov, O.; Shani, Z.; Levy, I., Carbohydrate binding modules: biochemical properties and novel applications. *Microbiology and Molecular Biology Reviews* 2006, 70 (2), 283-295.

[2] Goldstein, M. A.; Takagi, M.; Hashida, S.; Shoseyov, O.; Doi, R.; Segel, I., Characterization of the cellulose-binding domain of the *Clostridium cellulovorans* cellulose-binding protein A. *Journal of bacteriology* 1993, 175 (18), 5762-5768.

[3] Charreau, H.; L Foresti, M.; Vázquez, A., Nanocellulose patents trends: a comprehensive review on patents on cellulose nanocrystals, microfibrillated and bacterial cellulose. *Recent patents on nanotechnology* 2013, 7 (1), 56-80.

[4] Rebouillat, S.; Pla, F., State of the art manufacturing and engineering of nanocellulose: a review of available data and industrial applications. 2013.

[5] Peng, B.; Dhar, N.; Liu, H.; Tam, K., Chemistry and applications of nanocrystalline cellulose and its derivatives: a nanotechnology perspective. *The Canadian Journal of Chemical Engineering* 2011, 89 (5), 1191-1206.

[6] Shpigel, E.; Goldlust, A.; Eshel, A.; Ber, I. K.; Efroni, G.; Singer, Y.; Levy, I.; Dekel, M.; Shoseyov, O., Expression, purification and applications of staphylococcal Protein A fused to cellulose-binding domain. *Biotechnology and applied biochemistry* 2000, 31 (3), 197-203.

[7] U.S. Pat. No. 5,856,201.

[8] Marinaccio, P. J.; Repetti, R. V., Cross-flow filtration. Google Patents: 1989.

[9] Daufin, G.; Escudier, J.-P.; Carrere, H.; Berot, S.; Fillaudeau, L.; Decloux, M., Recent and emerging applications of membrane processes in the food and dairy industry. *Food and Bioproducts Processing* 2001, 79 (2), 89-102.

[10] Cheryan, M., *Ultrafiltration and Microfiltration Handbook*. Taylor & Francis: 1998.

[11] Azevedo, A. M.; Rosa, P. A.; Ferreira, I. F.; Aires-Barros, M. R., Chromatography-free recovery of biopharmaceuticals through aqueous two-phase processing. *Trends in biotechnology* 2009, 27 (4), 240-247.

[12] Thömmes, J.; Etzel, M., Alternatives to chromatographic separations. *Biotechnology progress* 2007, 23 (1), 42-45.

[13] Forsgren, A.; Sjöquist, J., "Protein A" from *S. aureus* I. Pseudo-immune reaction with human γ-globulin. *The Journal of Immunology* 1966, 97 (6), 822-827.

[14] Updyke, T. V.; Nicolson, G. L., Immunoaffinity isolation of membrane antigens with biotinylated monoclonal antibodies and immobilized streptavidin matrices. *Journal of immunological methods* 1984, 73 (1), 83-95.

[15] Stols, L.; Gu, M.; Dieckman, L.; Raffen, R.; Collart, F. R.; Donnelly, M. I., A new vector for high-throughput, ligation-independent cloning encoding a tobacco etch virus protease cleavage site. *Protein expression and purification* 2002, 25 (1), 8-15.

SUMMARY OF THE INVENTION

The inventors of the present invention have developed a method that exploits the combined features of carbohydrate binding modules (CBM) and nanocrystalline cellulose (CNC) for 'fishing out' specific agents of interest (AOI), e.g., proteins (POI—Protein Of Interest), which are optionally present or produced in culture. The method is based on the expression, in cell culture, of a CBM-protein chimera comprising of a CBM attached to a heterologous protein (HP) or an affinity domain with a strong affinity to the HP, followed by a series of filtration steps, wherein the attachment of CNC to the CBM part of the CBM-HP chimera enables the final isolation of the desired protein. As noted herein, the protein may be isolated in pure or substantially pure form of may be isolated as a fusion product.

Methods of the invention allow for fast, economical and efficient three stage purification/isolation method using filtration devices and technologies such as hollow-fiber, cross-flow filtration and others. The methods are based on reversible binding of a chimera composed of CBM and an AOI such as a protein, e.g., a heterologous protein (HP), to CNC, through the CBM part of the chimera by creating large protein/CNC adducts which are separated from contaminants by means of filtration, and can afterwards be used "as is". The CBM-AOI, e.g., CBM-protein chimera or CBM-HP chimera may be released from the CNC particles by various means, e.g., by varying the pH or by proteolysis and the protein, e.g., HP may be further separated from the CBM by various cleavage or separation techniques, as described hereinbelow.

The present invention is advantageous in that it combines the advantages of both hollow fiber separation processes and chromatographic separation processes, thereby enabling handling of very large volumes of solutions with a wide range of proteins and particulate matter, while providing a very high selectivity typically only encountered in affinity chromatography. The herein described methods avoid the need for column packaging and the involved limitations such as high pressures, low flow rates and clogging. While in affinity chromatography, the binding capacity of the resin to the target protein is up to 10 s of milligrams per 1 gram of resin, in the present invention, the capacity per 1 gr of CNC reaches 100 s of milligrams. Furthermore, the ability to selectively retain the target protein in the retentate while using microfiltration is a huge advantage as compared to ultrafiltration that is typically associated with high pressure, relatively slow filtration rate and clogging problems.

Thus, in one of its aspects, the present invention provides a method for isolating a protein such as a heterologous protein (HP) from a liquid mixture, the method comprising:
  passing a crude mixture comprising a CBM-protein chimera, e.g., CBM-HP chimera, through a first filtration membrane to obtain a permeate comprising the CBM-protein, e.g., CBM-HP (while leaving behind in the retentate high molecular weight or large size impurities that can be discarded);
  contacting the chimera, e.g., CMB-HP with CNC to allow interaction with the e.g., CBM-HP chimera, to obtain a mixture comprising a chimera-CNC complex, e.g., CBM-HP-CNC complex;
  filtering the mixture comprising the chimera-CNC complex, e.g., CBM-HP-CNC complex through a second filtration membrane to obtain a retentate comprising the complex; and
  optionally separating the CBM-HP and/or HP from CBM-HP-CNC complex for isolating the protein or HP;
  each of the first and second filtration membranes, being the same or different, having a pore size selected to permit permeation therethrough (or filtration or crossing) of the CBM-protein chimera and to prevent (or arrest) permeation of the complex.

In some embodiments, the present invention provides a method for isolating a heterologous protein (HP) from a liquid mixture, the method comprising:
  passing, filtering, a crude mixture comprising a CBM-HP chimera, through a first filtration membrane to obtain a permeate comprising the CBM-HP (while leaving behind in the retentate high molecular weight or large size impurities that can be discarded);
  contacting the CMB-HP chimera with CNC to allow interaction with the CBM-HP chimera, to obtain a mixture comprising a CBM-HP-CNC complex;
  passing, filtering, the mixture comprising the CBM-HP-CNC complex through a second filtration membrane to obtain a retentate comprising the CBM-HP-HP-CNC complex; and
  optionally separating the CBM-HP and/or HP from CBM-HP-CNC complex;
  each of the first and second filtration membranes, being the same or different, having a pore size selected to permit permeation therethrough (or filtration or crossing) of the CBM-HP chimera and to prevent (or arrest) permeation of the CBM-HP-CNC complex.

In some embodiments, the first and second filtration membranes are the same, and in some embodiments a single membrane is used in the method.

In some embodiments, the first and second filtration membranes are selected from hollow fiber membranes.

In some embodiments, the first and second filtration membranes are microfiltration membranes.

In some embodiments, the filtration membrane having a pore size of between 0.2 µm to 60 kDa.

In some embodiments, the method comprises obtaining a CBM-HP chimera in a crude mixture. In some embodiments, the CBM-HP is produced/expressed in a host cell, e.g., plant cells. In some embodiments, the CBM-HP is plant derived.

In some embodiments, the method comprises adding CNC to the permeate containing the CBM-HP chimera under conditions allowing interaction between the CBD-HP chimera and the CNC, to thereby obtain a mixture comprising the CBM-HP-CNC complex.

The term "heterologous protein" generally refers to a protein that is derived from the same or a different organism as compared to the organism from which it is produced (e.g., bacterial cell line transformed or transduced with a vector encoding a mammalian protein in a heterologous expression system). Heterologous proteins are typically produced by insertion of DNA encoding the protein, via recombinant DNA technology, into an expression vehicle which is used for transforming a host organism (e.g., yeast host cell). Some non-limiting examples of heterologous proteins are enzymes (e.g., nucleic acid modification enzymes) and substrate binding domains thereof, proteases, lymphokines, interferons, hormones and hormone precursors, polypeptides, peptides, antibodies and antibody fragments, antigens, antigenic epitopes and variants thereof, DNA binding proteins, receptors and fragments thereof, viral antigens or immunogens and any polypeptide and glycoprotein that can be expressed in a host organism that is different from the organism being the source of said protein. Thus, a chimera may be formed between the CBM and any one or more of enzymes (e.g., nucleic acid modification enzymes) and substrate binding domains thereof, proteases, lymphokines, interferons, hormones and hormone precursors, polypeptides, peptides, antibodies and antibody fragments, antigens, antigenic epitopes and variants thereof, DNA binding proteins, receptors and fragments thereof, viral antigens or immunogens and any polypeptide and glycoprotein that can be expressed in a host organism that is different from the organism being the source of said protein and others.

The HP may be in a crude mixture or medium, typically in the form of a "liquid mixture" that also comprises agents of impurity, products of competing reactions, cellular debris and/or a variety of other materials. The impurities from which the HP (or an agent of interest, as indicated below) is to be selectively isolated, may include any one or more of the following organic compounds (e.g., proteins, nucleic acids), cells, cellular components (macromolecules, cell debris), small molecules such as polyphenols; alkaloids; insoluble matter such as cell wall components (e.g., cellulose, lignin); viruses; bacteria; dust particles; salts; pesticides; and polymers such as starch and glycogen.

As used herein, the "CBM-HP chimera" (used interchangeable with fusion protein) generally refers to a protein made by joining together at least two proteins, one of which being a CBM and the other being HP. The CBM is a carbohydrate-binding module having a contiguous amino acid sequence within a carbohydrate-active enzyme, with a discreet fold having carbohydrate-binding activity. Some none-limiting examples of CBMs are carbohydrate-binding module family 1 to 83, as known in the art and available at the CAZy database for families of structurally related catalytic and carbohydrate-binding modules or functional domains of enzymes. CBMs may display substantial variation in substrate specificity, hence bind molecules such as monosaccharide (e.g., galactose, lactose, arabinose), glycosidic bond linkage and polysaccharides (e.g., cellulose, glucomannan, Xylan, starch, chitin) with various affinities.

In some embodiments, the CBM is a cellulose binding domain (CBD).

The CBD is a contiguous amino acid sequence module found within a protein that can bind cellulose/crystalline cellulose. When producing a CBD-HP chimera according to the invention, the CBD may be attached at the C-terminal or N-terminal of a protein. The CBM-HP chimera of the present invention, being in some embodiments a CBD-HP chimera, has a cellulose binding affinity (as measured by the dissociation constant [$K_d$]) of between about 0.5 μM and about 5 μM. The binding affinity may be maintained over a range of pH values and under different buffering conditions and can be reversed, e.g., to release the CBD from the CNC bound thereto, e.g., by elevating the pH to above about 11.

The HP may comprise more than one CBD units (e.g., one CBD unit at the C-terminus of the HP and another CBD unit at the N-terminus of the HP). In accordance with the present invention, the CBD protein may be a variant, derivative, fragment or chemical modification of any of the proteins or protein domains as described for example in the CAZy database, available at http://www.cazy.org/carbohydrate-binding-modules.html, as long as the fragment, derivative, variant or modification retain the CNC binding properties. In some embodiments, each CBD unit may be associated to one or more HP, which may be the same or different.

In some embodiments, the CBD protein is a CBD functional homolog having at least 70%, 80%, 90% or 95% homology to the amino acid sequence having the GeneBank accession numbers provided in http://www.cazy.org/carbohydrate-binding-modules.html. The term "homology" generally refers to a degree of complementarity with a reference sequence (e.g., a GeneBank SEQ ID NO) wherein a sequence may exhibit partial homology (e.g., 70% homology) or complete homology (i.e., 100% identity) to the reference sequence. The term "X % homology" (e.g. 70% homology) is not limited to sequences having the X % homology over the entire length of the protein. Thus, the 70% homology is also intended to include homology occurring in identified functional regions.

In some embodiments, the CBD is selected from CBM2 to CBM13, CBM16 to CBM17, CBM20 to CBM28, CBM40 to CBM46, and CBM61 to CBM67, as known in the art. For the sake of completion, the CAZY database provided in http://www.cazy.org/carbohydrate-binding-modules.html is incorporated herein by reference in its entirety.

In some embodiments, the functional region is a defined set of amino acids having the ability to bind cellulose with high affinity and in a reversible manner In some embodiments, the functional regions consist of about 200 amino acids. In some other embodiments, the functional regions consist of about 185 amino acids. In some other embodiments, the functional regions consist of about 50 amino acids.

In some embodiments, the CBD protein has the amino acid sequence of *Ruminiclostridium thermocellum*, having the GeneBank number EEU00265.1. In some embodiments, the CBD sequence is NLKVEFYNSNPSDTTNSINPQFKVTNTGSSAIDLSKLTL-RYYYTVDGQKDQTF WCDHAAIIGSNGSYN-GITSNVKGTFVKMSSSTNNADTYLEISFTGGTLEPGAH VQIQGRFAKNDWSNYTQSN-DYSFKSASQFVEWDQVTAYLNGVLVWGKEPG GSVVPSTQPVTTPPATTKPPATTIPP.

In some embodiments, the CBD is a CBD functional derivative.

As used herein, the term "CBD functional derivative" refers to any "fragment", "variant", "analogue" or "chemical derivative" of the CBD protein amino acid sequence shown in the GeneBank sequences above which retains the capability of binding to cellulose with high affinity and in a reversible manner.

In some embodiments, the CBD functional derivative is between about 2 and about 160 amino acids in length. In some other embodiments, the CBD functional derivative is between about 25 and about 125 amino acids in length. In still other embodiments, the CBD functional derivative is between about 50 and about 100 amino acids in length.

As used herein, the term "fragment" generally refers to a CBD protein derived from the CBD protein as defined herein, having a naturally occurring sequence. In some embodiments, the CBD fragment is produced by proteolytic cleavage of the full-length CBD protein. In other embodiments, the CBD fragment is obtained recombinantly by appropriately modifying the DNA sequence encoding the CBD protein by deleting one or more amino acids at one or more sites of the C-terminal, N-terminal, and/or within the naturally occurring sequence. In accordance with the present invention, fragments of the CBD used to produce the herein described, e.g., CDB-HP chimera, may be screened for the ability to bind cellulose with high affinity and in a reversible manner to determine the identity or utility of a functional derivative.

The "variant" is a molecule in which the amino acid sequence, glycosylation pattern, or other feature of a naturally occurring molecule has been modified covalently or non-covalently and is intended to include mutants. Some non-limiting examples of variants include amino acid substitutions, deletions, and/or insertions provided that the final construct possesses the desired ability of binding cellulose with high affinity and in a reversible manner.

Amino acid substitutions in the CBD protein may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, and tyrosine. The variant may also comprise additional amino acids at one or more sites of the C-terminal, N-terminal, and within the naturally occurring CBD sequence as long as the variant retains the capability of binding cellulose with high affinity and in a reversible manner.

The term "chemical derivative" generally refers to a CBD protein produced by chemical modification of naturally occurring or variant CBD protein. Some non-limiting examples of a chemical modification are replacement of H by, e.g., an alkyl, acyl, or amino group.

For producing the herein described CBD-HP chimera, a CBD encoding nucleic acid may be used to construct recombinant expression vectors capable of expressing the CBD protein or the CBD-HP chimera. The expression vectors (i.e. nucleic acid construct) used for expressing said chimera generally contain nucleotide sequences containing transcriptional and translational regulatory information, being operably linked (i.e., linked such that the regulatory DNA sequences and the DNA sequence to be expressed are connected in such a way as to permit transcription and ultimately translation of the RNA into the CBD-HP chimeric polypeptide). In accordance with the present invention, while constructing the CBD-HP chimera expression vector, the nucleic acid encoding the CBD protein is linked or joined to the nucleic acid encoding the HP such that the open reading frame of the CBD protein and the second protein is intact, allowing translation of the CBD fusion protein to occur. The CBD nucleic acid may be obtained from a variety of cell sources that produce cellulose binding domains that bind with high affinity and in a reversible manner or that produce CBD encoding mRNA.

In some embodiments, the nucleic acid encoding the CBD protein is obtained from *Clostridium cellulovorans.*

In other embodiments, the CBD encoding nucleic acid is obtained as described in U.S. Pat. No. 5,856,201, incorporated herein by reference.

In accordance with the invention, the nucleic acid encoding the CBD protein may be obtained from isolated and purified DNA from cell sources or by genomic cloning. When genetic cloning is the source of CBD protein, either cDNA or genomic libraries of clones may be prepared using techniques well known in the art. The libraries may be screened for particular CBD encoding nucleic acid with nucleotide probes that are substantially complementary to any portion of the gene. If detection of CBD protein encoding conserved nucleotide regions is desired, nucleotide probes are based on CBD nucleotide sequences conserved from species to species. If detection of CBD protein encoding unique nucleotide regions is desired, nucleotide probes are based on unique CBD nucleotide sequences. Alternatively, cDNA or genomic DNA may be used as templates for PCR cloning with suitable oligonucleotide primers. Full length clones, i.e., those containing the entire coding region of the desired CBD protein may be selected for constructing expression vectors, or overlapping cDNAs can be ligated together to form a complete coding sequence. Alternatively, CBD-encoding DNAs may be synthesized in whole or in part by chemical synthesis using techniques deemed to be standard in the art.

As readily understood by the skilled artesian, the selection of a suitable expression vector depends of various parameters, for example:
  whether it is to be used for nucleic acid amplification or for nucleic acid expression;
  the size of the nucleic acid to be inserted into the vector;
  the host cell to be transformed with the vector.

In accordance with the present invention, each vector may contain various components depending on its function (amplification of nucleic acid or expression of nucleic acid) and the host cell for which it is compatible.

The CBD-HP fusion protein may be obtained by subcloning a CBD-HP DNA into an expression vector (e.g. an *Escherichia coli* expression vector) that produces the CBD-HP chimeric fusion protein under the direction/control of the recombinant plasmid vector in a host cell (i.e. cell based culture system). The "host cell" (interchangeable herein with 'cell based culture system') is a cell type capable of growth in culture and capable of expressing a CBD protein or a CBD-HP chimera. The host cell may be cells grown in vitro culture including prokaryotic, eukaryotic, and insect cells. The host cell may be selected from a strain which modulates the expression of the inserted sequences, or modifies and processes the gene product in the specific fashion desired. For example, expression from certain promoters can be elevated in the presence of certain inducers (e.g., zinc and cadmium ions for metallothionine promoters). The host cell may be selected to secrete minimal amounts of proteolytic enzymes.

In some embodiments, the cell based culture system is a bacterial system selected from *Escherichia coli, Corynebacterium* and *Pseudomonas fluorescens*. In other embodiments, the cell based culture system is a eukaryotic system selected from Saccharomyces cerevisiae, Pichia Pastoris, Filamentous fungi, Baculovirus-infected cells, non-lytic insect cell expression and Leishmania. In other embodiments, the cell based culture system is a mammalian system selected from Chinese Hamster ovary (CHO) cell, human embryonic kidney (HEK) cells, Chinese Hamster ovary cells, mouse myeloma lymphoblstoid cells, human embryonic kidney cells (HEK-293), human embryonic retinal cells and human amniocyte cells (e.g. Glycotope and CEVEC). In still other embodiments, the cell based culture system is a cell-free system that contains all cellular components required for protein synthesis, wherein the proteins are produced in-vitro using purified RNA polymerase, ribosomes, tRNA and ribonucleotides.

The CBD or the CBD-HP chimera can be produced as described in U.S. Pat. No. 5,856,201, incorporated herein by reference.

Accordingly, the expression of the CBD protein or CBD-HP fusion protein may be controlled. The ability to control expression is important if the CBD protein or CBD-HP fusion protein is lethal to a host cell. In some embodiments, the HP is a recombinant protein prepared as a chimera with the CBD protein, wherein the CBD is fused to the N- or C-terminal of the HP. In some embodiments, the HP part of the chimera may be fused or joined to a third protein.

In some embodiments, the HP is prepared as a chimera with another element (e.g., streptavidin, Fc fragment, antigen and others) that can subsequently bind to CBM (or bind to CBM attached to the counterpart of the element). Thus, in accordance with the invention, the HP can be either directly attached to a CBM, for example when it is produced as a continuous amino acid stretch by recombinant means or it can bound to the CBM through another domain or interaction, e.g. protein A/Fc fragment, streptavidin/biotin etc. In some embodiments, the HP is connected to the CBM via a cleavage site (e.g. a TEV domain) or form a CBD-HP chimera.

In some embodiments, the CDM-HP chimera comprises at least one linker (e.g. a cleavable linker). The linker may have a length of between about 1 and 100 amino acids or between 2 to 20 amino acids, may be inserted between the CBM and the HP and may enhance the proteolytic stability of the CBD-HP chimera during its propagation in cell culture (e.g. during repeated passages).

The "crude mixture" from which the AOI, e.g., HP, is to be isolated as a chimera with CBD is generally a liquid cell culture mixture (i.e. host cell culture such as yeast or *E. coli* cell culture) that comprises a mixture of intact and fractionalized cells that are enriched with the herein defined CBD-HP protein chimera. The crude mixture may also contain other components (e.g. macromolecules) such as nucleic acids, proteins, carbohydrates, polyphenols and large non-polymeric molecules such as lipids. In some embodiments, the crude mixture is a homogenate formed by disrupting the cell membrane of cells contained in the cell culture.

The "filtration membrane" utilized in accordance with the invention is generally a micro-membrane that enables a flow-through of a (e.g. contaminated or crude) fluid to separate microorganisms and suspended particles contained in the fluid. The first and second filtration membranes may be the same or different and may have a pore size permitting permeation therethrough of the CBM-HP chimera, while preventing permeation of the CBM-HP-CNC complex, as defined. In some embodiments, the filtration membrane used in the process is the same for both filtration steps. In some embodiments, the filtration membrane having a pore size of between 0.2 μm to 60 kDa molecular weight cut off.

The membrane may be any suitable filtration membrane known in the field of the art that can act as a physical barrier that allows certain components (e.g., proteins) to pass through, depending on their physical and/or chemical properties. The filtration membrane is suitable to filtrate a desired molecule (e.g. a CDB-HP chimera) from the herein described crude mixture. The filtration membrane features adequate strength (e.g. to resist breaking and tearing during filtration) and sufficient hydrophilicity (to allow adequate wetting). In accordance with the present invention, the first molecular weight cutoff of the filtration membrane (i.e. the lowest molecular weight solute, in Daltons, in which 90% of the solute is retained by the membrane) is about 50 kDa.

In some embodiments, the filtration membranes used for any of the filtration steps may be the same and may be made, configured, constructed or used in a similar fashion. As the pore size of the membrane is said to be selected between 0.2 μm to 60 kDa molecular weight cut off, such a pore size selection is aimed at encompassing both microfiltration membranes having pore sizes ranging from 0.1 and 10 μm, as well as ultrafiltration members of pore sizes ranging from 0.1 and 0.01 μm. Alternatively, the filtration membranes may be selected based on their molecular weight cutoff, being no greater than 60 kDa.

Thus, the membranes may be selected to have a pore size of 0.2 and 10 μm or between 0.01 and 0.1 μm, or a molecular weight cutoff of up to 60 kDa.

In some embodiments, the lower membrane size is selected based on the pore size, being 0.2 μm, and the highest size is selected based on the molecular weight cutoff being no greater than 60 kDa.

In some embodiments, either or both filtration membranes has a pore size of between 0.45 μm to 60 kDa (molecular weight cut off). In other embodiments, the filtration membrane has a pore size of between 1 μm to 50 kDa (molecular weight cut off). In one embodiment, the filtration membrane has a pore size of about 0.2 μm.

The filtration membrane is used, in accordance with the present invention, to filter the herein described CBD-HP chimera (e.g. produced by recombinant processes) from the crude mixture containing the host cells that produced the chimera. The crude mixture typically comprises the CBD-HP chimera as well as various soluble and insoluble contaminants, as described herein. Thus, for example, at a molecular weight cut-off of about 300 kDa, the filtration membrane retains large particles and bacteria, wherein most globular proteins and small molecules easily permeate through along with the CBM-HP chimera. After most of the CBM-HP has been filtered through the membrane, the retentate (containing mostly pollutants) is discarded.

The filtration membranes may be selected amongst hollow fiber membranes, which may be of any material available in the art, such as ceramic hollow fiber membranes manufactured by Pall membralox, GEA, Novasep Kerasep and polymeric hollow fiber membranes manufactured by GE, Sartorius and others.

Following separation of the chimera, CNC (e.g. CNC particles) is added and allowed to interact with the chimera to obtain a CBM-HP-CNC complex, formed after binding of CNC to the CBM part of the CBM-HP chimera. In accordance with the present invention, the CNC may be added in the form a suspension of CNC particles in water or low conductivity phosphate buffer, wherein the concentration of CNC particles in the suspension is between about 0.01% and 10 wt % or between 0.5% and 2%.

In some embodiments, the binding of CNC to the CBM-HP chimera is carried out in a 10 mM phosphate buffer at pH 7.4.

In some embodiments, the CNC is incubated with the permeate containing the chimera for a period of between about 10 and mM and between about 240 minutes, in neutral pH (e.g. 1 to 100 mM phosphate buffer at pH 7.4) at a temperature of between 4 to 20° C., or about 4° C., prior to passing the mixture containing the CBM-HP-CNC complex through the filtration membrane.

The "crystalline nano-cellulose" (CNC) is a cellulose-derived material in the form of cellulose crystals having nanometer size range (in all dimensions, height, length and width). The CNC may be produced from any type of cellulose, including bacterial cellulose, plant cellulose, and others. In accordance with the invention, the CNC employed in the herein described methods may be from a commercially available source or prepared according to known methodologies such as the process described in WO 2012/014213 or its equivalent US application, herein incorporated by reference.

In some embodiments, the CNC is characterized by having at least 50% crystallinity. In some other embodiments, the CNC is monocrystalline. In some embodiments, the CNC is produced as particles (e.g., fibrils, or in other cases as crystalline material) from cellulose of various origins and is selected to be at least about 100 nm in length. In some embodiments, the CNC is at most about 1,000 μm in length. In other embodiments, the CNC particles are between about 100 nm and 1,000 μm in length, between about 100 nm and 900 μm in length, between about 100 nm and 600 μm in length, or between about 100 nm and 500 μm in length. In still other embodiments, the CNC particles are between about 100 nm and 1,000 nm in length, between about 100 nm and 900 nm in length, between about 100 nm and 800 nm in length, between about 100 nm and 600 nm in length, between about 100 nm and 500 nm in length, between about 100 nm and 400 nm in length, between about 100 nm and 300 nm in length, or between about 100 nm and 200 nm in length.

In accordance with the present invention, the thickness of the CNC may be between about 5 nm and 100 nm and the CNC may be selected to have an aspect ratio (length-to-diameter ratio) of 10 and more. In some embodiments, the aspect ratio is between 67 and 100. In some embodiments, the CNC is selected to be between about 100 nm and 400 nm in length and between about 5 nm and 30 nm in thickness.

In accordance with a method of the invention, the mixture comprising a CBM-HP-CNC (e.g. CBD-HP-CNC) complex is passed through a different or same filtration membrane, which due to the increase in size does not permit the CBD-HP-CNC complex to permeate through. The permeate (e.g. containing various plant proteins) is discarded and the retentate containing the (purified) CBM-HP-CNC complex is then treated to isolate or separate the HP. The separation of HP from the CBM-HP-CNC complex can be carried out using various chemical procedures (e.g. elution using pH elevation, proteolysis) that are common to the field of the art. For example, the release of CBM-HP chimera from the CNC particles may be achieved by elevating the pH to thereby obtain CBM-HP chimera which after proteolysis with a suitable proteolytic enzyme releases the HP from the CBM-HP chimera. In some embodiments, the isolation of HP may be carried out by elevating the pH to about a pH level of 11 to 12 to release the CBM-HP chimera from the NCC followed by the addition of at least one proteolytic enzyme to release CBM from the HP. Some non-limiting examples of proteolytic enzyme are Tobacco Etch Virus nuclear-inclusion-a endopeptidase (TEV), Factor X, Enterokinase, Thrombin HRV-3C, ficin and papain.

The HP obtained in the method of the invention can be used to "fish out" an agent of interest (AOI) that may be an amino acid based or non-amino acid based agent. Thus, the method may further comprise a step of allowing interaction between an isolated HP or an HP chimera, e.g., CBM-HP chimera, and at least one AOI. The AOI may be any agent or material capable of affinity binding to the HP. Such agents may be selected from amino acid based agents, wherein the HP is an antibody, receptor, enzyme, substrate and the like or a fragment thereof; a nucleic acid based agent, wherein the HP is a nucleic acid binding protein or a fragment thereof; a sugar, a fatty acid or a small organic molecule having a peptide moiety capable of affinity binding to it.

Thus, in another one of its aspects the present invention provides a method for isolating an agent of interest (AOI) from a liquid mixture, the method comprising:
treating a medium comprising at least one AOI with a CBM-HP chimera (that is optionally obtained and isolated in accordance with a method of the invention as defined hereinabove; or that is prepared and isolated aby any other fashion) under conditions permitting association between the AOI and CBM-HP chimera to obtain a mixture comprising a CBM-HP-AOI complex;
adding CNC to the mixture comprising the CBM-HP-AOI complex to form a CNC-CBM-HP-AOI complex;

passing the mixture comprising the CNC-CBM-HP-AOI complex through a filtration membrane not permitting permeation of the CNC-CBM-HP-AOI complex, to obtain a retentate comprising the CNC-CBM-HP-AOI complex; and isolating the AOI from the complex.

The filtration membrane may be defined as above.

In some embodiments, the method further comprises a step of obtaining a medium comprising the AOI to be isolated. In some embodiments, the medium is a crude mixture, as defined herein, containing the AOI, and thus may be passed through a filtration membrane having a pore size of about 0.2 microns to partially clear out impurities from the medium.

Figures 1A, 1B:
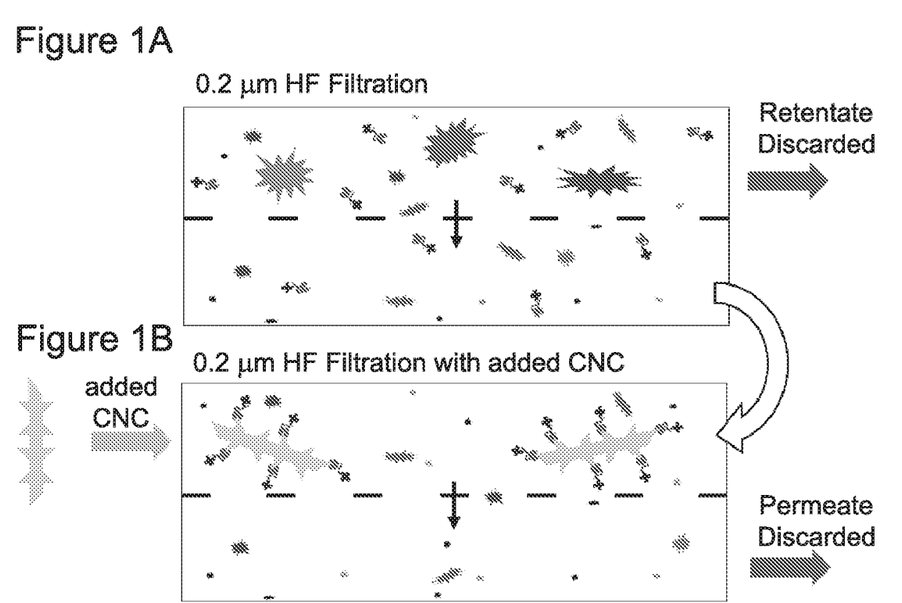
FIGS. 1A-1E provide a schematic illustration of an isolation method according to the invention.
Figure 1C:
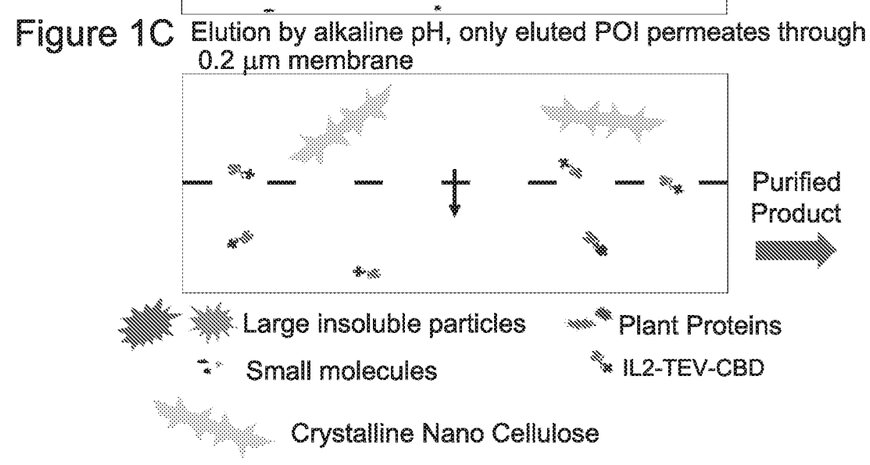

To isolate/separate the AOI from the CNC-CBD-HP-AOI complex, a variety of chemical procedure common to the field of the art can be executed. For example, the AOI can be released by lowering the pH to a pH of between 1.5 to 3, adding a specific salt such as NaCl, Guanidinium chloride or a metal acetate such as a lithium acetate or solvent such as ethanol and n-butanol. The AOI has to pass through the membrane after the release and thus cleared from the solution In some embodiments, the mixture comprising the CNC-CBM-HP-AOI complex is further purified by means of further dialysis (separating molecules in solution by the difference in their rates of diffusion through a semipermeable membrane) or filtration before isolating the AOI from the CNC-CBD-HP-AOI complex.

In some embodiments, the retentate (mixture) comprising the CNC-CBM-HP-AOI complex is collected and stored for further processing when required.

In other embodiments, to release the CNC form the CNC-CBM-HP-AOI complex or CNC-CBM-HP complex obtained in the methods of the invention, the pH of the mixture comprising the complex is elevated to between about 10 and between about 13. According to such embodiments, the CNC may be discarded or recycled and the CBM-HP-AOI complex can be collected (e.g. by filtration).

In other embodiments, to isolate the pure HP, a suitable protease, as described herein, may be used. According to such embodiments, the linker protein present between the CBM protein and the HP protein is digested and the HP can thus permeate through the membrane and be collected in the permeate. The CNC-CBM complex is discarded with the retentate.

In still other embodiments, when an AOI is to be isolated from a CNC-CBM-HP-AOI complex, wherein HP is affinity-bound to the AOI (e.g. being another protein, small molecule nucleic acid sequence etc.), the HP and AOI bond is cleaved using a suitable chemical procedure (e.g. pH or salt concentration change). Thus, for example, if an antibody (being an AOI) bound to protein A (being the HP) that is linked to CBM-CNC, a low pH will only release the antibody from protein A, but not the CBD from the CNC.

In some embodiments, the CBM is a CBD, as defined herein.

In accordance with the invention, any of the filtration steps in methods described herein may be repeated at least once (e.g. employing several buffer volumes) until the desired purity is achieved.

A schematic representation of a method according to the invention is provided in FIGS. 1A-1E, wherein as shown in FIG. 1A a crude mixture containing both the chimera and pollutants of all sizes is filtered, e.g., with a 0.2 µm membrane. Only large insoluble particles are retained and may be discarded once all the chimera has permeated. The permeate containing the chimera is then contacted, as shown in FIG. 1B, with CNC that is added to the mixture and after a short incubation period is filtered through a different, similar or an identical filtration membrane, e.g., a 0.2 µm membrane. Only small soluble molecules and pollutant proteins permeate and are discarded. As shown in FIG. 1C, once a desired purity is reached, the pH is elevated, and the CBD is released from the NCC particles. The chimera (e.g., of a protein of interest, POI) is free to permeate through the membrane and is collected. The retentate (now containing only NCC) is discarded.

Figure 1D:
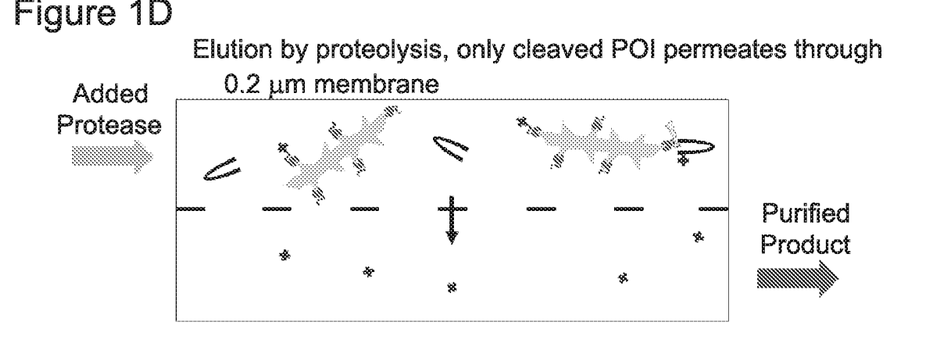
Figure 1E:
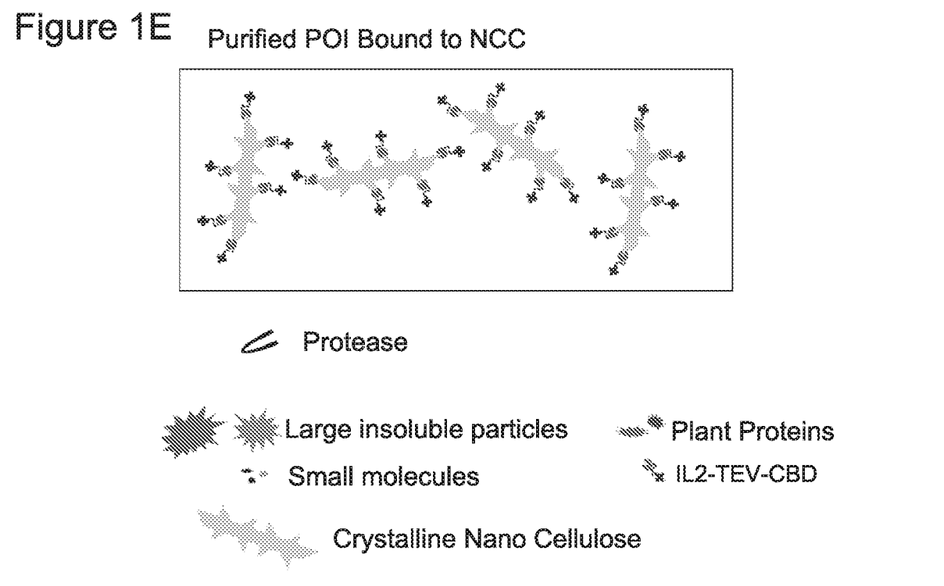

If only a pure chimera is desired, without the CBD moiety, as shown in FIG. 1D, a suitable proteolytic enzyme may be added. After breaking the connection between the CBD and the AOI/HP (e.g., POI), the CBD remains bound to the NCC and the AOI/HP (e.g., POI) is free to permeate through the membrane and is collected. However, if, as shown in FIG. 1E, the NCC-CBD-HP/AOI complex is desired (e.g., NCC-IL-2-TEV-CBD), it can be collected directly after Stage B. Thus, the invention further provides a method for isolating HP from a liquid mixture, the method comprising:
  passing a crude mixture comprising a chimera of at least one carbohydrate-binding module and at least one HP (CBM-HP chimera) through a first filtration membrane to obtain a permeate comprising the CBM-HP chimera;
  contacting the CBM-HP chimera with cellulose nanocrystals (CNC) to allow interaction with the CBM-HP chimera, to obtain a mixture comprising a CBM-HP-CNC complex;
  passing the mixture comprising the CBM-HP-CNC complex through a second filtration membrane to obtain a retentate comprising the CBM-HP-CNC complex; and
  separating the HP and/or the CBM-HP chimera from the CBM-HP-CNC complex;
  the first and second filtration membranes, being the same or different, having a pore size selected to permit permeation therethrough of the CBM-HP chimera and to prevent permeation therethrough of the CBM-HP-CNC complex.

In some embodiments, the method further comprising obtaining the CBM-HP chimera in a crude mixture so that it may be isolated therefrom. In some embodiments, the crude mixture further comprising at least one other material selected from nucleic acids, proteins, carbohydrates, polyphenols and large non-polymeric molecules. In some embodiments, the crude mixture is a homogenate formed by disrupting the cell membrane of cells contained in a cell culture.

In some embodiments, the CBM-HP chimera is produced or expressed in a host cell.

In some embodiments, the CBM-HP chimera is produced in plant cells.

In some embodiments, the method further comprising isolating the CBM-HP chimera, and/or the HP. In some embodiments, CBM-HP chimera is first isolated and subsequently the HP therefrom.

In some embodiments, the method further comprising treating a liquid medium comprising at least one agent of interest (AOI) with the CBM-HP chimera under conditions permitting association between the at least one AOI and the CBM-HP chimera to obtain a mixture comprising a CBM-HP-AOI complex.

In some embodiments, the method comprising isolating the AOI from the CBM-HP-AOI complex.

In some embodiments, the CBM is a cellulose binding domain (CBD).

In some embodiments, the first and second filtration membranes are the same.

In some embodiments, the CBM-HP chimera is a CBD-HP chimera.

In some embodiments, the HP is isolated in a form suitable for use in a method of isolating an agent of interest.

The invention further provides a method for isolating an agent of interest (AOI) from a liquid mixture, the method comprising:
  obtaining a CBM-HP chimera according to a method of the invention;
  treating a liquid medium comprising at least one AOI with the CBM-HP chimera under conditions permitting association between the at least one AOI and CBM-HP chimera to obtain a mixture comprising a CBM-HP-AOI complex;
  adding CNC to the mixture comprising the CBM-HP-AOI complex to form a CNC-CBM-HP-AOI complex;
  passing the mixture comprising the CNC-CBM-HP-AOI complex through a filtration membrane having a pore size not permitting permeation of the CNC-CBM-HP-AOI complex, to obtain a retentate comprising the CNC-CBM-HP-AOI complex; and
  isolating the AOI from the complex.

The invention further provides a method for isolating an agent of interest (AOI) from a liquid mixture, the method comprising:
  treating a liquid medium comprising at least one AOI with a CBM-HP chimera under conditions permitting association between the at least one AOI and CBM-HP chimera to obtain a mixture comprising a CBM-HP-AOI complex;
  adding CNC to the mixture comprising the CBM-HP-AOI complex to form a CNC-CBM-HP-AOI complex;
  passing the mixture comprising the CNC-CBM-HP-AOI complex through a filtration membrane having a pore size not permitting permeation of the CNC-CBM-HP-AOI complex, to obtain a retentate comprising the CNC-CBM-HP-AOI complex; and included
  isolating the AOI from the complex.

BRIEF DESCRIPTION OF FIGURES

The following figures demonstrate certain advantageous features of the present invention. It is stressed that the particulars shown are by way of example and for purposes of illustrative discussion of the embodiment of the invention.

DETAILED DESCRIPTION OF EMBODIMENTS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

In one of its main aspects the invention provides a method for obtaining of a heterogeneous protein present in a liquid mixture the method comprising:

producing the heterogeneous protein (HP) attached to a cellulose binding domain (CBD) in a first crude mixture;

passing the first crude mixture through a first filtration membrane having a first cutoff of 60 kDa (UF range.) to 0.45 microns (MF range) and discarding the retentate composed of large polluting particles to obtain the permeate;

adding to the permeate of (2) CNC particles to obtain a second mixture;

Passing the second mixture of (3) through a second filtration membrane having a cutoff of up to 0.45 microns and thereby obtaining the purified heterogeneous protein attached to the CNC particles.

The heterogynous protein (HP) may be the protein of interest that needs to be obtained at the end of the product, for example a recombinant protein prepared as a chimera with the CBD protein, or prepared as a chimera with another element (streptavidin, Fc fragment, antigen. etc.) that can subsequently bind to CBD (or bind to CBD attached the counterpart of the element).

The HP is may be used to "fish out" an agent of interest (that may be amino acid based or non-amino acid based agent) from a crude mixture.

In accordance with this second aspect, the present invention concerns obtaining an agent of interest present in a liquid mixture that is capable of affinity binding to a heterogeneous protein, the method comprising:

adding to the liquid mixture the heterogeneous protein (HP) attached to a cellulose binding domain (CBD) in a first crude mixture;

either before or after the addition of the CBD-HP chimera passing the first crude mixture through a first filtration membrane having a first cutoff of 10 kDa (UF) to 0.45 microns (MF range) and discarding the retentate composed of large polluting particles to obtain the permeate;

adding to the permeate of (2) CNC particles to obtain a second mixture;

Passing the second mixture of (3) through a second filtration membrane having a cutoff of up to 0.45 microns and obtaining the retentate thereby obtaining the agent of interest.

It should be noted in step 2 that it is preferable to add the CBD-HP chimera after the first filtration, thereby enabling usage of a lower cutoff membrane and hence improving purification.

The method may further include additional steps, that are known in the art for separating the affinity binding of the agent of interest and the heterogeneous protein, including but not limited to pH adjustment, ionic adjustment, addition of chaotropic or cosmotropic agents, urea, organic solvents or detergents, sugars, nucleotides (e.g. ATP), temperature adjustment or excised affinity binding domains. Any added materials can be later discarded by means of further dialysis or filtration.

The agent of interest (AOI) capable of affinity binding to the heterogeneous protein may be an amino acid bases agent (the HP being an antibody, receptor, enzyme, substrate and the like or a fragment thereof), a nucleic acid based agent (and the HP being a nucleic acid binding protein or a fragment thereof), a sugar, fatty acid small organic molecule which have an amino acid based molecule (being the HP) capable of affinity binding to it.

The following passages are relevant both in connection with the first and second options Generally, the first membrane and the second membrane are the same having a cutoff of 0.2 microns.

The membranes may be hollow-fiber or cross-flow filtration membranes.

The HP is either directly attached to a CBD, for example produced as a continuous amino acid stretch by recombinant means or bound to it through another domain or interaction, e.g. protein A/Fc fragment, streptavidin/biotin etc. It is also possible to connect the HP to the CBD via a cleavage site, such as TEV domain. This will form a CBD-HP chimera.

The retentate obtained at step (4) of the method of the invention may further be processed by the following:

If the entire CNC-CBD-HP complex is desired, it can simply be collected.

If the CBD-HP chimera is the desired product, and the CNC should be discarded the pH is elevated to about pH 10.5-13, the proteins are quickly released and permeate through the membrane to be collected. The CNC particles are discarded (as their cost in negligible) or are recycled.

If only the pure HP is desired, a suitable protease is added to the solution, and digests the linker protein between the CBD protein and the HP protein, thus releasing the HP from the CBD that remains bound to the NCC. The freed HP is now able to penetrate through the membrane and gets collected in the permeate, and the CNC-CBD complex is discarded with the retentate.

Separation of the HP from the excised CBD is necessary only in a very specific case were the CBD-HP chimera is excised and the CBD released from the CNC; otherwise the CBD remains bound to the CNC and discarded with it.

If indeed the chimera is first released from the CNC and afterwards digested, the separation can be performed with the aid of chromatography or other separation methods that depend on specific protein biochemical properties.

The present invention is advantageous in that it combines together benefits from both membranal separation processes and chromatographic separation processes: it can handle very large volumes of solutions with a wide range of proteins and particulate matter while providing a very high selectivity only encountered in affinity chromatography. It avoids the need for column packaging, and the involved limitations such as high pressures, low flow rates and clogging.

Typically in affinity chromatography, the binding capacity of the affinity chromatography resin to the target protein is up to 10 s of milligrams per 1 gram of resin. In the current invention, the capacity of 1 gr of CNC reach 100 s of milligrams per 1 gram of CNC. Furthermore, the ability to selectively retain the target protein in the retentate while using microfiltration is a huge advantage compared to ultrafiltration that is typically associated with high pressure, relatively slow filtration rate and clogging problems.

The described purification method allows for fast, economical and efficient three stage protein purification using existing filtration devices and technologies such as hollow-fiber and cross-flow filtration etc. The method of the present invention is based on reversible binding of a chimera composed of Cellulose Binding Domain (CBD) and heterogonous protein (HP)—to Crystalline Nano Cellulose (CNC), through the CBD part of the chimera and thus creating large protein/CNC adducts. The adducts are separated from the contaminants by means of filtration, and are afterwards used "as is", or the chimera (CBD-HP) is released from the CNC particles by pH change or proteolysis, or the HP is separated from the CBD by various cleavage or separation techniques as will be explained below The HPs have to be either directly attached to a CBD or bound to it through another domain or interaction, e.g. protein A/Fc fragment, streptavidin/biotin etc. It is also possible to connect the HP to the CBD via a cleavage site, such as TEV domain. This will form a CBD-HP chimera.

The heterogynous protein (HP) may be the protein of interest that needs to be obtained at the end of the product, for example a recombinant protein prepared as a chimera with the CBD protein, or prepared as a chimera with another element (streptavidin, Fc fragment, antigen) that can subsequently bind to CBD (or CBD having the counterpart of the element).

Alternatively the HP be a protein (antibody or fragment, receptor or fragment, substrate binding domain of an enzyme, substrate, DNA binding protein etc.) that is capable of affinity binding to a protein of interest present in the sample that needs to be separated.

The CBD-HP chimera can be produced for example by recombinant processes and needs to be purified from the crude mixture in which it was prepared. In such a case the crude mixture that contains the CBD-HP chimera and contaminants from various types and sizes (both soluble and insoluble) is first filtered through a 0.1-0.45, preferably a 0.2 µm micro-filtration membrane, preferably hollow fiber membrane or cross-flow device. At this cut off the membrane retains large particles and bacteria, but most globular proteins and small molecules easily permeate through with the CBD-HP chimera. After most of the CBD-HP has been separated, the retentate (now containing mostly pollutants) is discarded.

If the CBD-HP is intended to "fish" from a crud mixture a protein of interest (that affinity binds to the HP part of the chimera) the same steps as above may be done, or alternatively, first the crude mixture of filtered through a 0.1-0.45, preferably a 0.2 µm micro-filtration membrane, preferably hollow fiber membrane or cross-flow device. At this cut off the membrane retains large particles and bacteria, but most globular proteins, and only after this step the CBD-HP is added.

In the second stage CNC is added, CBD-HP binds CNC particles and forms large adducts that are now larger than the cutoff of the membrane 0.1-0.45, preferably 0.2 µm membranal cutoff and cannot penetrate the membrane. They are therefore retained in the retentate while all other contaminating small molecules and proteins are removed. Any number of buffer volumes can be exchanged until the desired purity is achieved.

In the last stage the product is harvested. This could be performed in one of four ways:

In cases where the HP is the protein of interest (for example produced in recombinant techniques):
1. If the entire CNC-CBD-HP complex is desired, it can simply be collected.
2. If the CBD-HP chimera is the desired product, and the CNC should be discarded the pH is elevated to about pH 10.5-11, the proteins are quickly released and permeate through the membrane to be collected. The CNC particles are discarded (as their cost in negligible) or are recycled.
3. If only the pure HP is desired, a suitable protease is added to the solution, and digests the linker protein between the CBD protein and the HP protein, thus releasing the HP from the CBD that remains bound to the NCC. The freed HP is now able to penetrate through the membrane and gets collected in the permeate, and the CNC-CBD complex is discarded with the retentate.
4. In cases where the HP is affinity bound to another agent (another protein, small molecule nucleic acid sequence etc.) that is the agent of interest, the affinity binding between the HP and agent of interest is broken either when the HP is still as in (1) above or separated as in 2 or 3 above for example by pH or salt concentration change. Suitable conditions have to be defined, in which only the affinity binding is broken, without release of the CBD from the CNC.

Crystalline nano-cellulose (CNC As used herein) refers cellulose crystals in nanometer size range in all dimensions (length and width), from any type of cellulose, including bacterial cellulose, plant cellulose etc.

In some embodiments, the nano-cellulose material is characterized by having at least 50% crystallinity. In further embodiments, the nano-cellulose material is monocrystalline.

In some embodiments, the nano-cellulose material, produced as particles (e.g., fibrils, or in other cases as crystalline material) from cellulose of various origins, is selected to be at least about 100 nm in length. In other embodiments, they are at most about 1,000 µm in length. In other embodiments, the nano-cellulose material particles are between about 100 nm and 1,000 µm in length, between about 100 nm and 900 µm in length, between about 100 nm and 600 µm in length, or between about 100 nm and 500 µm in length.

In some embodiments, the CNC particles are between about 100 nm and 1,000 nm in length, between about 100 nm and 900 nm in length, between about 100 nm and 800 nm in length, between about 100 nm and 600 nm in length, between about 100 nm and 500 nm in length, between about 100 nm and 400 nm in length, between about 100 nm and 300 nm in length, or between about 100 nm and 200 nm in length. The thickness of the CNC may vary between about 5 nm and 100 nm.

The fibrils of the CNC may be selected to have an aspect ratio (length-to-diameter ratio) of 10 and more. In some embodiments, the aspect ratio is 67-100.

The NCNC is selected to be between about 100 nm and 400 nm in length and between about 5 nm and 30 nm in thickness.

The NCC may be used as commercially available or may be prepared according to known methodologies such as the process described in WO 2012/014213 or its equivalent US application, herein incorporated by reference.

CBD Protein

The CBD protein may be a variant, derivative, fragment or chemical modification of any of the proteins or protein domains as appear in http://www.cazy.org/carbohydrate-binding-modules.html, as long as the fragment, derivative, variant or modification retain the CNC binding properties.

The CBD protein of the present invention is one having at least 70% homology to the amino acid sequence as in the above GenBank accession numbers, preferably, at least 80% homology, more preferably, at least 90% homology, and most preferably, at least 95% homology. The term "X % homology" is not intended to be limited to sequences having an X % homology over the entire length of the protein. The 70% homology is also intended to include X % homology occurring in identified functional areas within the CBD protein of the above Genebank accession numbers. An example of a functional area would be a defined set of amino acids having the ability to bind cellulose with high affinity and in a reversible manner. Such protein homologs may also be referred to herein as "CBD functional homologs." In one embodiment of the present invention, such a functional area may have about 100 amino acids. In another embodiment of the present invention, such a functional area may have about 50 amino acids. The most desirable CBD protein of the present invention is one comprised of the amino acid sequence indicated above The term "CBD functional derivative" as used herein refers to any "fragment", "variant", "analogue" or "chemical derivative" of the CBD protein amino acid sequence shown in the Genebank sequences indicated above which retains the capability of binding to cellulose with high affinity and in a reversible manner and is preferably between about 2 and about 160 amino acids in length, more preferably between about 25 and about 125 amino acids in length and most preferably between about 50 and about 100 amino acids in length.

The term "fragment" is used to indicate a CBD protein which is derived from the CBD protein shown in, and has a naturally occurring sequence. Such a fragment may be produced by proteolytic cleavage of the full-length protein. Alternatively, the fragment is obtained recombinantly by appropriately modifying the DNA sequence encoding the CBD protein to delete one or more amino acids at one or more sites of the C-terminal, N-terminal, and within the naturally occurring sequence. Fragments of the CBD protein can be screened for the ability to bind cellulose with high affinity and in a reversible manner to determine the identity or utility of a functional derivative.

The term "variant" as used herein is defined as a molecule in which the amino acid sequence, glycosylation pattern, or other feature of a naturally occurring molecule has been modified covalently or non-covalently and is intended to include mutants. Some of the variants falling within this invention possess amino acid substitutions deletions, and/or insertions provided that the final construct possesses the desired ability of binding cellulose with high affinity and in a reversible manner. Amino acid substitutions in the CBD protein may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine. Also included within the definition of variant are those proteins having additional amino acids at one or more sites of the C-terminal, N-terminal, and within the naturally occurring CBD sequence as long as the variant retains the capability of binding cellulose with high affinity and in a reversible manner.

The term "chemical derivative" as used herein refers to a CBD protein produced by chemical modification of naturally occurring or variant CBD protein. Illustrative of an example of a chemical modification would be replacement of H by an alkyl, acyl, or amino group.

CBD-HP Chimera

The term "CBD-HP chimera" as used herein refers to the joining together of at least two proteins, a CBD protein and a second protein being the HP. In some embodiments of the present invention, the HP may be fused or joined to a third protein. In the present invention, examples of HP's include enzymes, such as nucleic acid modification enzymes, proteases, hormones or hormone precursors, polypeptides, peptides, antibodies, antigens, antigenic epitopes and variants thereof.

CBD encoding nucleic acid may be used to construct recombinant expression vectors capable of expressing the CBD protein or the CBD-HP chimera of the present invention. A nucleic acid construct is capable of expressing a protein if it contains nucleotide sequences containing transcriptional and translational regulatory information and such sequences are "operably linked" to nucleotide coding sequences. "Operably linked" refers to a linkage in which the regulatory DNA sequences and the DNA sequence to be expressed are connected in such a way as to permit transcription and ultimately translation.

In constructing the CBD-HP chimera expression vector, the nucleic acid encoding the CBD protein is linked or joined to the nucleic acid encoding the HP such that the open reading frame of the CBD protein and the second protein is intact, allowing translation of the CBD fusion protein to occur. CBD nucleic acid may be obtained from a variety of cell sources that produce cellulose binding domains that bind with high affinity and in a reversible manner or that produce CBD encoding mRNA. The preferred source of CBD encoding nucleic acid is *Clostridium cellulovorans*. The CBD encoding nucleic acid may be obtained as described in U.S. Pat. No. 5,856,201 incorporated herein by reference.

The nucleic acid encoding the CBD protein of the present invention may be obtained from isolated and purified DNA from cell sources or by genomic cloning. Either cDNA or genomic libraries of clones may be prepared using techniques well known in the art and may be screened for particular CBD encoding nucleic acid with nucleotide probes that are substantially complementary to any portion of the gene. If detection of CBD protein encoding conserved nucleotide regions is desired, nucleotide probes should be based on CBD nucleotide sequences conserved from species to species. If detection of CBD protein encoding unique nucleotide regions is desired, nucleotide probes should be based on unique CBD nucleotide sequences. Alternatively, cDNA or genomic DNA may be used as templates for PCR cloning with suitable oligonucleotide primers. Full length clones, i.e., those containing the entire coding region of the desired CBD protein may be selected for constructing expression vectors, or overlapping cDNAs can be ligated together to form a complete coding sequence. Alternatively, CBD-encoding DNAs may be synthesized in whole or in part by chemical synthesis using techniques deemed to be standard in the art.

Many vectors are available, and selection of the appropriate vector will depend on various factors, such as, but not limited to the factors provided below: 1) whether it is to be used for nucleic acid amplification or for nucleic acid expression, 2) the size of the nucleic acid to be inserted into the vector, and 3) the host cell to be transformed with the vector. Each vector contains various components depending on its function (amplification of nucleic acid or expression of nucleic acid) and the host cell for which it is compatible.

The term "host cell" refers to those cells capable of growth in culture and capable of expressing a CBD protein or CBD-HP chimera. The host cells of the present invention encompass cells in in vitro culture and include prokaryotic, eukaryotic, and insect cells. A host cell strain may be chosen which modulates the expression of the inserted sequences, or modifies and processes the gene product in the specific fashion desired. Expression from certain promoters can be elevated in the presence of certain inducers (e.g., zinc and cadmium ions for metallothionine promoters. Therefore expression of the CBD protein or CBD fusion protein may be controlled. The ability to control expression will be important if the CBD protein or CBD fusion protein is lethal to a host cell. Modifications (e.g., phosphorylation) and processing (e.g., cleavage) of protein products are important for the function of the protein. Different host cells have characteristic and specific mechanisms for the post-translational processing and modification of protein. Appropriate cell lines or host systems can be chosen to ensure the correct modification and processing of the CBD protein or CBD fusion protein expressed. Preferably, the host cell should secrete minimal amounts of proteolytic enzymes Other details for producing the CBD or the CBD-HP chimera can be found in publication U.S. Pat. No. 5,856,201 incorporated herein by reference.

The invention claimed is:

1. A method for isolating a heterologous protein (HP) from a liquid mixture, the method comprising:
    passing a crude mixture comprising a chimera of at least one carbohydrate-binding module and at least one HP (CBM-HP chimera) through a first filtration membrane to obtain a permeate comprising the CBM-HP chimera;
    contacting the CBM-HP chimera with cellulose nanocrystals (CNC) to allow interaction with the CBM-HP chimera, to obtain a mixture comprising a CBM-HP-CNC complex;
    passing the mixture comprising the CBM-HP-CNC complex through a second filtration membrane to obtain a retentate comprising the CBM-HP-CNC complex; and
    separating the HP and/or the CBM-HP chimera from the CBM-HP-CNC complex;
    the first and second filtration membranes, being the same or different, having a pore size selected to permit permeation therethrough of the CBM-HP chimera and to prevent permeation therethrough of the CBM-HP-CNC complex.

2. The method according to claim 1, comprising obtaining the CBM-HP chimera in a crude mixture, wherein the crude mixture optionally further comprises at least one other material selected from nucleic acids, proteins, carbohydrates, polyphenols and large non-polymeric molecules.

3. The method according to claim 2, wherein the CBM-HP chimera is produced or expressed in a host cell or is produced in plant cells.

4. The method according to claim 1, comprising isolating the CBM-HP chimera, and isolating the HP subsequently from the CBM-HP chimera.

5. The method according to claim 4, further comprising treating a liquid medium comprising at least one agent of interest (AOI) with the CBM-HP chimera under conditions permitting association between the at least one AOI and the CBM-HP chimera to obtain a mixture comprising a CBM-HP-AOI complex.

6. The method according to claim 5, comprising isolating the AOI from the CBM-HP-AOI complex.

7. The method according to claim 1, wherein the CBM is a cellulose binding domain (CBD).

8. A method for isolating an agent of interest (AOI) from a liquid mixture, the method comprising:
    obtaining a CBM-HP chimera according to a method of claim 1;
    treating a liquid medium comprising at least one AOI with the CBM-HP chimera under conditions permitting association between the at least one AOI and CBM-HP chimera to obtain a mixture comprising a CBM-HP-AOI complex;
    adding CNC to the mixture comprising the CBM-HP-AOI complex to form a CNC-CBM-HP-AOI complex;
    passing the mixture comprising the CNC-CBM-HP-AOI complex through a filtration membrane having a pore size not permitting permeation of the CNC-CBM-HP-AOI complex, to obtain a retentate comprising the CNC-CBM-HP-AOI complex; and
    isolating the AOI from the complex.

9. A method for isolating an agent of interest (AOI) from a liquid mixture, the method comprising:

treating a liquid medium comprising at least one AOI with a CBM-HP chimera under conditions permitting association between the at least one AOI and CBM-HP chimera to obtain a mixture comprising a CBM-HP-AOI complex;

adding CNC to the mixture comprising the CBM-HP-AOI complex to form a CNC-CBM-HP-AOI complex;

passing the mixture comprising the CNC-CBM-HP-AOI complex through a filtration membrane having a pore size not permitting permeation of the CNC-CBM-HP-AOI complex, to obtain a retentate comprising the CNC-CBM-HP-AOI complex; and isolating the AOI from the complex.

10. The method according to claim 8, further comprising obtaining a medium comprising the AOI from which the AOI is to be isolated.

11. The method according to claim 9, further comprising obtaining a medium comprising the CBM-HP chimera.

12. The method according to claim 1, wherein the first filtration membrane and the second filtration membrane, being same or different, each having a pore size of between 0.2 μm to 60 kDa molecular weight cut off.

13. The method according to claim 1, wherein the CBM is CBD and is selected from CBM2-13, CBM16-17, CBM20-28, CBM40-46 and CBM61-67.

14. The method according to claim 13, wherein the CBD is a CBD functional derivative.

15. The method according to claim 14, wherein the CBD is associated to more than one HP, each HP may optionally be different from the other.

16. The method according to claim 1, wherein the HP part of the CBM-HP chimera is prepared as a chimera with another element that subsequently binds to CBM.

17. The method according to claim 1, wherein the HP of the CBM-HP chimera is bound to the CBM through another domain or interaction.

18. The method according to claim 1, wherein the CBM-HP chimera comprises at least one linker.

19. The method according to claim 8, wherein the AOI is selected from the group consisting of an amino acid based agent; a nucleic acid based agent a sugar, a fatty acid and an organic molecule having a peptide moiety capable of affinity binding to the HP;

wherein when the AOI is an amino acid based agent, the HP is an antibody, receptor, enzyme, substrate or a fragment thereof; and wherein when the AOI is a nucleic acid based agent, the HP is a nucleic acid binding protein or a fragment thereof.

* * * * *